Oct. 28, 1975
H. W. MOTZKAU
AZALEA PLANT
Filed Oct. 30, 1975
Plant Pat. 3,795
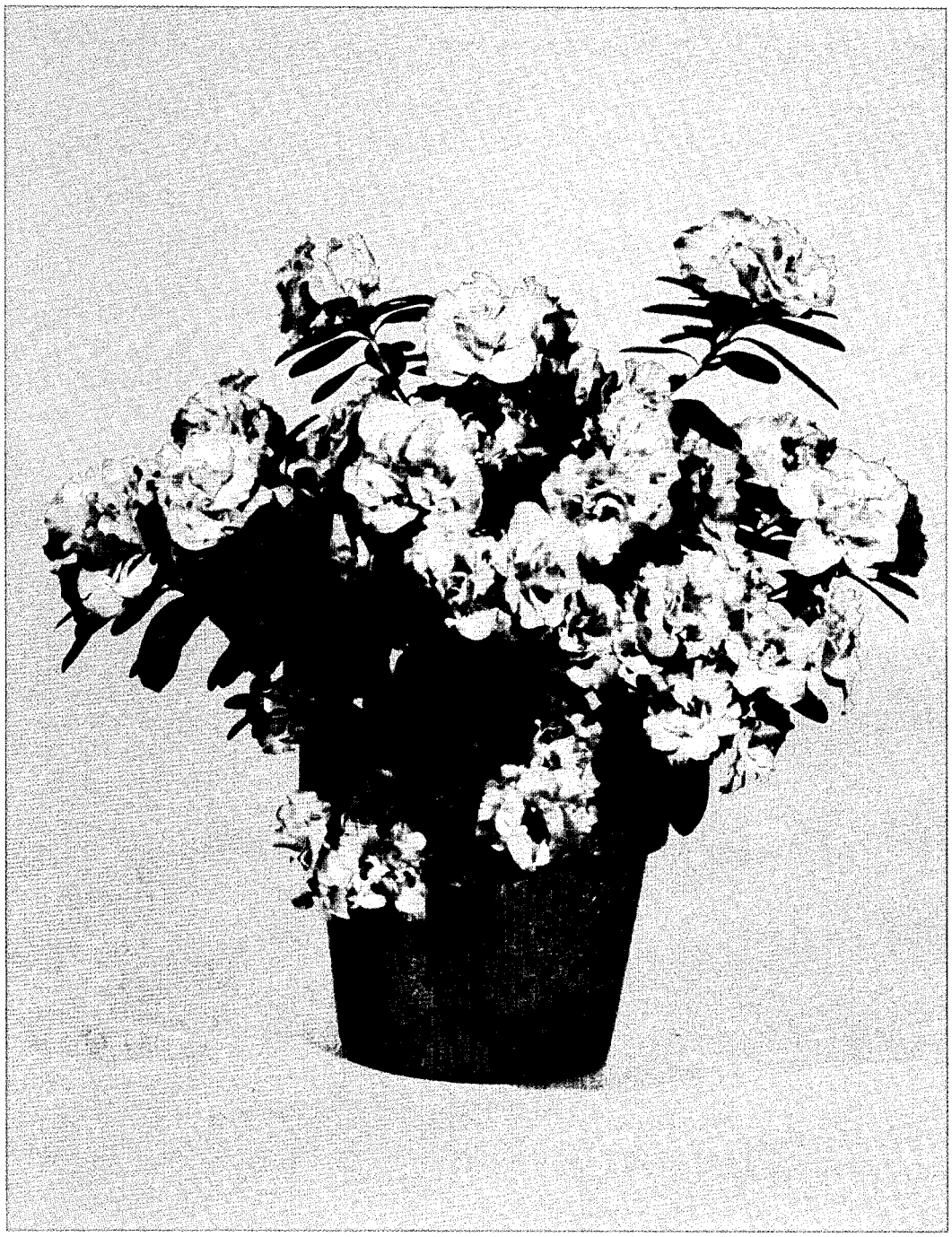

United States Patent

Plant Pat. 3,795
Patented Oct. 28, 1975

1

3,795
AZALEA PLANT

Henry W. Motzkau, Rte. 5, Oak Drive,
Berryville, Ark. 72616

Filed Oct. 30, 1974, Ser. No. 519,269
Int. Cl. A01h 5/00
U.S. Cl. Plt.—57 1 Claim The present invention comprises a new and distinct variety, a greenhouse forcing type azalea plant of the Rhododendron genus, hereinafter referred to as Prize.

Prize was originated in a controlled breeding program in Whitewater, Wis., in the year 1967. The female, or seed parent, was #1645, an unnamed seedling with red semi-double flowers which was originated from a cross by the present inventor between an unidentified seedling with red flowers and #965 Vivien, an unpatented seedling with red double flowers.

The male, or pollen parent, was #1040 Kingfisher, a commercially available, unpatented variety with deep pink, semi-double flowers which was originated by the present inventor from an unidentified cross.

The new cultivar Prize was discovered and selected as a seedling within a flowering progeny of the stated cross by Henry W. Motzkau in 1969 in a controlled environment at Whitewater, Wis.

Prize was a product of a planned breeding program which had as its objective the creation of greenhouse forcing azaleas that would fulfill in part or in whole the need for improved growth and breaking action, improved durability or keeping quality, shorter dormancy requirements and more intense vibrant red color.

This first act of asexual production of the original seedling selection was completed when vegetative cuttings were taken in 1969 by Henry W. Motzkau in a controlled environment at Whitewater, Wis.

Continued asexual reproduction by vegetative cuttings for evaluative flowering programs have demonstrated that the combination of characteristics as herein disclosed for the variety Prize are firmly fixed and are retained through successive generations.

The following description is based on observations and measuresments made under stated environments in Barberton, Ohio. Plant material utilized was produced under greenhouse environments with conditions that closely approximate those generally used in commercial practice as defined in Chart A which appears at the end of the present specification.

The phenotype of Prize may vary significantly with variations in environment such as temperature, day length, and light intensity. When an environment divergent from that presented in Chart A was utilized to more clearly define a trait, that environment is specified. The behavior of the genotype of Prize was not observed under all possible environments.

Prize was evaluated as a greenhouse forcing azalea and has been found to bud, cool, and flower uniformly during all seasons of the year in controlled daylength and temperatuer environments. Natural season response is classified as early or December flowering.

Commercially available varieties of similar type with which Prize may be compared are Kingfisher and Roadrunner.

(1) The dark rose pink flower color of Prize, when compared to that of Roadrunner, is distinguished by being a brighter color with less of the blue overtones which are present in the flower color of Roadrunner.

(2) The dark rose pink flower color of Prize, when compared to that of Kingfisher, is distinguished by being a more intense color with stronger red overtones.

The following traits have been repeatedly observed and are determined to be basic characteristics of Prize which

2 in combination distinguish this azalea as a new and distinct variety:

(1) General tonality of dark rose pink flower color.

(2) Semi-double to double flower form.

(3) Medium flower size averaging 2.75 inches in diameter.

(4) Early natural season response (normally flowering for Christmas from an early July final pinch with fall natural cooling with temperatures as low as 40° F. until November 20, followed by forcing with minimum night temperatures of 60° F.).

(5) Consistent average development of two flowers per terminal cluster.

(6) Rapid uniform response in year round controlled flowering programs.

(7) Average of up to 21 days of flower retention for high keeping quality.

(8) Durable, leathery foliage of high gloss.

The accompanying photographic drawing shows typical flower and foliage characteristics of Prize. Colors are as nearly true as possible with color illustrations of this type. Color references are made to The Munsell Limit Color Cascade, 1972 edition. Details of time, place and light conditions are provided whenever possible.

Botanical classification: Hybrid of Rhododendron genus.

Perianth:

*Color.*—General tonality: rose pink, 41–11 [1]. Calyx: rose pink, 40–3 [2]. Corolla: Opening stages: rose pink, 41–11 [1]. Abaxial (fully open): rose pink, 41–9 [1] to approximately 41–11 [2], but more grey. Adaxial (fully open): rose pink, 41–9 [1] to approximately 41–11 [2], but more grey. Blotch: dark rose pink, 42–12 [1] to 40–13 [2]. Discoloration: rose pink, 41–9 [1], retains color approximately 21 days followed by gradual fading.

Bud:

*Size.*—Medium.

*Form.*—Conoidal.

Bloom:

*Size.*—Average 2¾". Range: 2½"–3½".

*Borne.*—Several together in terminal clusters. Average: 2½". Range: 2"–3".

*Form.*—Semi-double to fully double with varying numbers of petaloid anthers.

*Response.*—Natural season: early, Christmas. Year round: early.

*Bud sheath.*—Pubescent; persistent.

*Calyx.*—Semi-petaloid; pubescent.

*Peduncle.*—¾" in length; pubescent.

*Petals.*—Form: Arrangement: imbricate. Fragrance: none. Persistence: non-shatter. Longevity (keeping quality): greenhouse: 21 days. Home: 28 days.

Reproductive organs:

*Stamen.*—5–10. Filaments: columnar; 40–4 [3]. Anthers: 40–7 [3].

*Pistil.*—Stigma: generally columnar, occasionally fasciated; color approximately 30–4 [3]. Style: generally columnar, occasionally fasciated; color approximately 40–6 [3]. Ovaries: superior; velutinous.

Foliage:

*Type.*—Evergreen.

*Leaves.*—Single; obovate form with mucronate apices and obtuse bases; abaxially and adaxially strogose.

[1] Color values determined approximately Apr. 15, 1974. No time or light intensity values were recorded. Barberton, Ohio.

[2] Color values determined Aug. 9, 1974, between 3:00 p.m. and 3:30 p.m., under fluorescent lighting (approximately 175 ft. candles). Barberton, Ohio.

*Color.*—New foliage: abaxial: 19–15 [3]. adaxial: approximately 21–11 [3] overlaid with white. Mature foliage: abaxial: 21–14 [3]. adaxial: approximately 21–11 [3] overlaid with white.

Plant:

*Growth habit.*—Semi-upright bush.

CHART A.—AZALEA YEAR ROUND SCHEDULE

| Minimum night temperature—65° F. | | | | | Minimum temp. 45° F.—Cool | Minimum night temperature—65° F. | |
|---|---|---|---|---|---|---|---|
| | | Lights | | | | | |
| Plant | Pinch | On | Off | Shade* | | Force | Flower |
| 1/19/71 | 1/26/71 | 1/26 | 3/15 | 4/6 | 5/18 | 6/28 | 7/27 |
| 3/2 | 3/9 | ---------- | | 5/18 | 6/29 | 8/10 | 8/7 |
| 4/13 | 4/20 | ---------- | | 6/22 | 8/3 | 9/14 | 10/19 |
| 5/25 | 6/1 | ---------- | | 8/3 | 9/14 | 10/19 | 11/30 |
| 7/6 | 7/13 | 9/5 | 9/21 | —(9/14) | 11/2 | 12/14 | 1/18/72 |
| 8/17 | 8/24 | 9/5 | 10/26 | —(10/19) | 12/14 | 1/18/72 | 2/2/72 |
| 9/28 | 10/5 | 10/5 | 11/30 | —(12/8) | 2/1/72 | 3/14 | 4/18 |
| 11/9 | 11/6 | 11/16 | 1/25/72 | —(1/25) | 3/21 | 5/2 | 5/30 |
| 12/21 | 12/28 | 12/28 | 3/7 | —(3/7) | 4/25 | 6/6 | 7/4 |
| 2/1/72 | 2/8/72 | 2/8 | 3/28 | 4/18 | 5/30 | 7/11 | 8/8 |
| 3/14 | 3/21 | ---------- | | 5/30 | 7/11 | 8/22 | 9/19 |
| 4/25 | 5/2 | ---------- | | 7/4 | 8/15 | 9/26 | 10/31 |
| 6/6 | 6/13 | ---------- | | 8/15 | 9/26 | 11/7 | 12/12 |
| 7/18 | 7/25 | 9/5 | 9/19 | —(9/19) | 11/7 | 12/19 | 1/23/73 |
| 8/29 | 9/5 | 9/5 | 11/7 | —(11/7) | 12/26 | 2/6 | 3/13 |
| 10/10 | 10/17 | 10/17 | 12/19 | —(12/9) | 2/13/73 | 3/27 | 5/1 |
| 11/21 | 11/28 | 11/28 | 1/30/73 | —(1/30) | 4/3 | 5/15 | 6/12 |

*Figures in parenthesis are shade dates if there is light interference in greenhouse.

[3] Color values determined Aug. 13, 1974, between 11:00 a.m. and 1:30 p.m. under fluorescent lighting (approximately 90 ft. candles). Barberton, Ohio.

I claim:

1. A new and distinct variety of azalea characterized particularly as to novelty by its general tonality of dark rose pink flower color; semi-double to double flower form; medium flower size averaging 2.75 inches in diameter; early natural season response, normally flowering for Christmas from an early July final pinch with fall natural cooling with temperatures as low as 40° F. until November 20 followed by forcing with minimum night temperatures of 60° F.; consistent average development of two flowers per terminal cluster; rapid uniform response in year round controlled flowering programs; average of up to 21 days of flower retention for high keeping quality, and its durable, leathery foliage of high gloss.

No references cited.

ROBERT E. BAGWILL, Primary Examiner